United States Patent [19]

Bristow et al.

[11] Patent Number: 4,933,171
[45] Date of Patent: Jun. 12, 1990

[54] ORAL COMPOSITIONS

[75] Inventors: Neil J. Bristow, New South Wales, Australia; Peter Carter, Burton, Great Britain; Bryony E. Coulson, Port Sunlight, Great Britain; Michael A. Trevethan, Bebington, Great Britain

[73] Assignee: Unilever Patent Holdings B.V., Rotterdam, Netherlands

[21] Appl. No.: 354,658

[22] Filed: May 19, 1989

[30] Foreign Application Priority Data

May 19, 1988 [GB] United Kingdom ................. 8811830

[51] Int. Cl.$^5$ ................................. A61K 7/16
[52] U.S. Cl. ......................... 424/57; 424/49
[58] Field of Search .................... 424/49, 57

[56] References Cited

U.S. PATENT DOCUMENTS

| 3,699,221 | 4/1972 | Gubner | 424/49 |
| 3,863,066 | 1/1975 | Honosh | 424/49 |
| 4,011,309 | 3/1977 | Lutz | 424/49 |
| 4,132,773 | 1/1979 | Best et al. | 424/57 |
| 4,327,079 | 4/1982 | Aoki | 424/57 |
| 4,631,185 | 12/1986 | Kim | 424/49 |
| 4,634,589 | 1/1987 | Scheller | 424/49 |
| 4,751,072 | 6/1988 | Kim | 404/49 |

FOREIGN PATENT DOCUMENTS

| 680108 | 1/1968 | Canada . |
| 999238 | 11/1976 | Canada . |
| 0029332 | 5/1981 | European Pat. Off. . |
| 166055 | 2/1986 | European Pat. Off. . |
| 222603 | 5/1987 | European Pat. Off. . |
| 278744 | 8/1988 | European Pat. Off. . |
| 283231 | 9/1988 | European Pat. Off. . |
| 2602981 | 7/1977 | Fed. Rep. of Germany . |
| 1586915 | 3/1981 | United Kingdom . |
| 87/07615 | 9/1982 | World Int. Prop. O. . |

Primary Examiner—Shep K. Rose
Attorney, Agent, or Firm—Milton L. Honig

[57] ABSTRACT

The present invention relates to oral compositions for treating sensitive teeth.

These compositions comprise an agent for desensitizing sensitive teeth, such as potassium nitrate of strontium acetate, and a particulate abrasive material which is hydroxyapatite. The hydroxyapatite is compatible with the desensitizing agent.

5 Claims, No Drawings

ORAL COMPOSITIONS

This invention relates to oral compositions and in particular to oral compositions containing an agent for desensitising sensitive teeth.

It is an object of the invention to provide an improved tooth desensitising composition, The novel tooth desensitising oral composition of this invention comprises a combination of insoluble and soluble compounds each having a tooth desensitizing action and wherein the insoluble compound also acts as a tooth cleaning and polishing agent.

Accordingly, the invention provides a tooth desensitising oral composition comprising a finely divided hydroxyapatite and a source of potassium and/or strontium ions.

It is already known to use finely divided hydroxyapatite as an abrasive of an oral composition (see CA-A No. 999 238, U.S. Pat. Nos. 4,634,589 and 4,327,079) but its use in products containing a source of potassium and/or strontium ions has not previously been suggested.

The hydroxyapatite abrasive is used in a particle size giving satisfactory cleaning without being harmful to the tooth surface when used in appropriate amounts in dentifrices of the invention. The average particle size will usually be in the range from about 1 micron to about 15 microns, preferably 2-10 and particularly preferably about 3 to about 10 microns.

Preferred particulate hydroxyapatites for use in oral compositions of this invention are synthetic hydroxyapatites of high purity consisting of at least 92% of $Ca_{10}(PO_4)_6(OH)_2$. The remainder will comprises mainly bound water (typically 6% maximum) and a minor amount of calcium carbonate (typically 2% maximum). A process for the preparation of hydroxyapatites is described in GB-A No. 1 586 915 (British Charcoals & Macdonalds).

A highly pure synthetic hydroxyapatite available commercially is that sold under the trade name CAPTAL by British Charcoals & Macdonalds of Greenock, Scotland. This hydroxyapatite contains about 97% $Ca10(PO_4)6(OH)2$ The remaining 3% is mostly bound water with approximately 0.3% calcium carbonate.

The amount of the hydroxyapatite present in oral compositions of this invention will range from 1-50%, usually about 2% to about 20%, preferably 3 to 15%, by weight of the oral composition.

Various potassium and strontium compounds have been described in the literature for use as tooth desensitising agents. U.S. Pat. No. 3,863,006 (Hodosh) describes the use of potassium nitrate. EP-A No.95 871 (Reckitt and Colman) discloses the use of potassium citrate. PCT/US85/00123 (The Trustees of Columbia University in the City of New York) discloses the use of potassium bicarbonate and potassium chloride. A further effective potassium compound which is disclosed in our co-pending application No. 8706187 is potassium acetate.

U.S. Pat. No. 3,122,483 (Block Drug Co.) discloses the use of water-soluble strontium compounds as tooth desensitising agents, such as strontium chloride, strontium lactate, strontium acetate, strontium bromide, strontium iodide, strontium nitrate and strontium salicylate. U.S. Pat. No. 3,699,221 (Schole et al.) describes the use of a non-toxic, water-soluble ionic strontium compound selected from the class consisting of organic chelating agents and inorganic sequestering agents. Examples of such agents are strontium citrate, disodium salt of ethylenediamine tetraacetic acid, strontium gluconate and strontium gentisate.

The amount of the source of potassium or strontium ions will generally be from about 1% to about 20%, usually to about 10%, for example from 2% to 8%, more preferably 3-6% by weight of the oral composition.

An additional benefit which is already associated with the use of hydroxyapatite in the prior literature is a remineralising effect on tooth material.

Together with the hydroxyapatite and the source of potassium or strontium ions, the oral product of the invention will contain other conventional ingredients well known to those skilled in art depending on the form of the oral product. For instance, in the case of an oral product in the form of a dentifrice cream or paste, the product will comprise an humectant-containing liquid phase and a binder or thickener which acts to maintain the particulate solid abrasive in stable suspension in the liquid phase. A surfactant and a flavouring agent are also usual ingredients of commercially acceptable dentifrices.

Humectants commonly used are glycerol and sorbitol syrup (usually comprising an approximately 70% solution). However, other humectants are known to those in the art, including propylene glycol, lactitol and hydrogenated corn syrup. The amount of humectant will generally range from about 10 to 85% by weight of the dentifrice. The remainder of the liquid phase will consist substantially of water.

Likewise, numerous binding or thickening agents have been indicated for use in dentifrices, preferred ones being sodium carboxymethylcellulose and xanthan gum. Others include natural gum binders such as gum tragacanth, gum karaya and gum arabic, Irish moss, alginates and carrageenans. Silica thickening agents include the silica aerogels and various precipitated silicas. Mixtures of binding and thickening agents may be used. The amount of binder and thickening agent included in a dentifrice is generally between 0.1 and 10% by weight.

It is usual to include a surfactant in a toothpaste and again the literature discloses a wide variety of suitable materials. Surfactants which have found wide use in practice are sodium lauryl sulphate, sodium dodecylbenzene sulphonate and sodium lauroylsarcosinate. Other anionic surfactants may be used as well as other types such as cationic, amphoteric and non-ionic surfactants. Surfactants are usually present in an amount of from 0.5 to 5% by weight of the dentifrice.

Flavours that are usually used in dentifrices are those based on oils of spearmint and peppermint. Examples of other flavouring materials used are menthol, clove, wintergreen, eucalyptus and aniseed. An amount of from 0.1% to 5% by weight is a suitable amount of flavour to incorporate in a dentifrice.

The oral compositions of the invention may also comprise a proportion of a supplementary abrasive agent such as silica, alumina, hydrated alumina, calcium carbonate, anhydrous dicalcium phosphate, dicalcium phosphate dihydrate and water-insoluble sodium metaphosphate.

The oral composition of the invention may include a wide variety of optional ingredients. These include an anti-plaque agent such as an antimicrobial compound, for example chlorhexidine or 2,4,4'-trichloro-2'-hydroxy-diphenyl ether, or a zinc compound (see EP- No. 161 898); an anti-tartar ingredient such as a condensed phosphate, e.g. an alkali metal pyrophosphate, hexametaphosphate or polyphosphate, (see U.S. Pat. Nos. 4,515,772 and 4,627,977) or zinc citrate (see U.S. Pat. No. 4,100,269); a fluorine-containing compound such as sodium fluoride or sodium monofluorophosphate; sweetening agent such as saccharin; an opacifying agent, such as titanium dioxide, a preservative, such as formalin; a colouring agent; or pH-controlling agent such as an acid, base or buffer, such as benzoic acid.

For a fuller discussion of the formulation of oral compositions, reference is made to Harry's Cosmeticology, Seventh Edition, 1982, Edited by J. B. Wilkinson and R. J. Moore, pages 609 to 617.

The invention also relates to a method of desensitising sensitive teeth which consists in applying to the teeth, such as by brushing, an oral composition according to the invention.

The following Examples illustrate the invention. Percentages and parts are by weight.

EXAMPLE 1

A toothpaste is prepared from the following ingredients:

| Ingredient | % |
| --- | --- |
| Hydroxyapatite | 5.00 |
| Silica aerogel (Gasil 23) | 10.00 |
| Sorbitol syrup | 40.00 |
| Sodium lauryl sulphate | 1.50 |
| Sodium carboxymethylcellulose | 1.00 |
| Potassium nitrate | 3.00 |
| Sodium monofluorophosphate | 0.76 |
| Sodium saccharin | 0.20 |
| Titanium dioxide | 1.00 |
| Formalin | 0.04 |
| Flavour | 1.00 |
| Water | to 100.00 |

EXAMPLE 2

A toothpaste is prepared from the following ingredients:

| Ingredient | % |
| --- | --- |
| Hydroxyapatite | 5.00 |
| Silica aerogel (Gasil 23) | 10.00 |
| Sorbitol syrup | 40.00 |
| Sodium lauryl sulphate | 1.50 |
| Sodium carboxymethylcellulose | 1.00 |
| Strontiu chloride | 5.00 |
| Sodium monofluorophosphate | 0.76 |
| Sodium saccharin | 0.20 |
| Titanium dioxide | 1.00 |
| Formalin | 0.04 |
| Flavour | 1.00 |
| Water | to 100.00 |

EXAMPLES 3 TO 6

Toothpastes are made from the ingredients indicated below.

| Ingredient | % Example 3 | 4 | 5 | 6 |
| --- | --- | --- | --- | --- |
| Hydroxyapatite | 10.0 | 10.0 | 5.0 | 5.0 |
| Thickening silica | 10.0 | 10.0 | 10.0 | 10.0 |
| Sorbitol syrup (708 solution) | 40.0 | 40.0 | 40.0 | 40.0 |
| Sodium lauryl sulphate | 1.5 | 1.5 | 1.5 | — |
| Sodium carboxymethylcellulose | 1.0 | 1.0 | 1.0 | 1.0 |
| Potassium nitrate | 3.0 | — | 3.0 | 3.0 |
| Strontium acetate | — | 3.0 | — | — |
| Sodium monofluorophosphate | 0.8 | 0.8 | 0.8 | 0.8 |
| Triclosan | 0.2 | — | — | — |
| Hexetidine | — | 0.2 | — | — |
| Polyethyleneglycol 300 | 6.0 | — | — | — |
| Chlorhexidine digluconate | — | — | 0.1 | 0.1 |
| Stannous chloride | — | — | 0.4 | 0.4 |
| Sodium saccharin | 1.2 | 0.2 | 0.2 | 0.2 |
| Titanium dioxide | 1.0 | 1.0 | 1.0 | 1.0 |
| Formalin | 0.04 | 0.04 | 0.04 | 0.04 |
| Flavour | 1.0 | 1.0 | 1.0 | 1.0 |
| Water | all to 100.0 | 100.0 | 100.0 | 100.0 |

We claim:

1. An oral composition for the treatment of sensitive teeth, comprising a source of potassium and/or strontium ions as desensitising agent, and a particulate abrasive material, wherein the particulate abrasive material is or comprises hydroxyapatite.

2. A preparation according to claim 1, wherein the hydroxyapatite has an average particle size of from 1 to 15 microns.

3. A preparation according to claim 1, wherein the hydroxyapatite is a synthetic hydroxyapatite which consists for at least 92% by weight of $Ca_{10}(PO_4)_6(OH)_2$.

4. A preparation according to claim 1, wherein the hydroxyapatite is present in an amount of 1–50% by weight.

5. A composition according to claim 1, wherein the composition comprises from 1–10% by weight of the source of the potassium and/or strontium ions as desensitising agent.

* * * * *